US006769624B2

(12) United States Patent
Herman et al.

(10) Patent No.: US 6,769,624 B2
(45) Date of Patent: Aug. 3, 2004

(54) METHOD OF SUPPLYING STABLE, NON-FOGGING FRAGRANCES TO VEHICLES

(75) Inventors: Stephen J. Herman, Totowa, NJ (US); Richard N. H. Neill, Atlanta, GA (US)

(73) Assignee: Aromatic Fragrances & Flavors, Marietta, GA (US)

( * ) Notice: Subject to any disclaimer, the term of this patent is extended or adjusted under 35 U.S.C. 154(b) by 324 days.

(21) Appl. No.: 09/781,184

(22) Filed: Feb. 13, 2001

(65) Prior Publication Data

US 2003/0015598 A1 Jan. 23, 2003

(51) Int. Cl.$^7$ ................................................ B05B 17/00
(52) U.S. Cl. ........................... 239/1; 239/337; 239/338
(58) Field of Search ................................ 239/34–60, 6, 239/337, 338, 1

(56) References Cited

U.S. PATENT DOCUMENTS

| | | | | | |
|---|---|---|---|---|---|
| 4,027,068 | A | * | 5/1977 | Saad | ........................ 428/426 |
| 4,381,246 | A | * | 4/1983 | Anderson | ..................... 252/91 |
| 4,906,488 | A | * | 3/1990 | Pera | ............................. 426/573 |
| 5,716,921 | A | * | 2/1998 | Neumiller | .................... 510/181 |
| 6,048,265 | A | * | 4/2000 | Apple | ......................... 454/157 |
| 6,114,298 | A | * | 9/2000 | Petri et al. | ................... 510/372 |
| 6,194,498 | B1 | * | 2/2001 | Anderson et al. | ........... 524/168 |
| 6,279,834 | B1 | * | 8/2001 | Fox et al. | ...................... 239/3 |

* cited by examiner

*Primary Examiner*—Dinh Q. Nguyen

(57) ABSTRACT

A method of producing stable, non-fogging fragrances for automobiles and other vehicular environments. A non-fogging fragrance constructed by combining ingredients individually passing a standard fogging test. Non-fogging solvents identified to maintain a liquid fragrance and prevent freezing at low temperatures. The fragrance chemically stabilized by storage in a tightly sealed container covered with an inert gas. The sealed container also eliminates unwanted vapor emissions in the vehicle. The fragrance is provided on demand as a spray, ensuring delivery with uniform odor integrity over the lifetime of the product.

9 Claims, No Drawings

METHOD OF SUPPLYING STABLE, NON-FOGGING FRAGRANCES TO VEHICLES

FIELD OF THE INVENTION

The field of the invention is a process for providing an acceptable fragrance into automobiles and other vehicles, both ground and air. The process provides stable odor over time in a uniform formulation that does not deposit on the surface of glass or plastic, causing unacceptable fogging.

BACKGROUND OF THE INVENTION

The use of fragrant materials in environmental areas has a long history. Many patents exist for devices for applying fragrance to the air of buildings and vehicles. They primarily deal with mechanisms of application rather than the chemical and physical properties of the aromas themselves. Specifically, no prior patent concerns the creation of aromas satisfying all the requirements of the automotive industry.

Fragrances are complicated mixtures of chemicals that if exposed to air for extended periods of time undergoes significant alteration in odor. There are two major reasons for this change. The first is the fact that the so-called top note of the fragrance is composed of compounds that volatilize rapidly, and become depleted from the fragrance composition. The second is the fact that many fragrance compounds undergo oxidation when exposed to air. This oxidation results in a state sometimes referred to as rancidity. These two pathways result in an unacceptable change in the fragrance over time.

The methods of dispensing odors often involve evaporation from a substrate such as a paper blotter or plastic film. Such methods result in the release of selective components over time, continually changing the odor character. Spraying the aroma by pump or aerosol delivers a fragrance of uniform quality over time, and this is the preferred method of this invention.

The area in which there is a long felt need for improved fragrance delivery is within the automobile. The automobile offers a number of challenges to applying fragrance over an extended time. The first is the fact that fragrance compositions exposed to the air will undergo loss of top note and be susceptible to rancidity. The second is the fact that fragrance compounds will condense on the glass in an automobile, giving a phenomenon known as fog.

The Society of Automotive Engineers has advanced a test method (SAE J1756) which is applied to all materials used in the automobile. This method, entitled "Test procedure to determine the fogging characteristics of interior automotive materials", is used on all products that are used inside automobiles. Standard fragrances contain many compounds that do not pass this test either alone or in combination with others.

SAE J1756 tests the tendency of interior materials used in automobiles and other vehicles to produce a light-scattering film (fog) on a glass surface or to produce a measurable deposit on aluminum foil. Fog is defined as the deposit of an undesirable light-scattering film on the interior glass surface of a vehicle. Fog Number, determined by a photometric method, is the quotient, expressed as the 60 degree reflectance value of a glass plate with fogging deposits and the 60 degree reflectance of the same glass plate without fogging deposits, multiplied by 100. The basic components of the fog test unit are a chamber that can be heated, and a glass plate that can be cooled.

The need for a fragrance delivery system and compositions for such delivery that is (a) chemically uniform with time, (b) is resistant to oxidation and rancidity, and (c) will pass the SAE J1756 test, has not been recognized by the fragrance industry. It was not until the process of the present invention that compositions passing the SAE J1756 test as well as methods for their delivery were attained.

Fragrances are not one component systems: rather they are typically complex mixtures of ingredients that interact with each other to produce an appealing odor. It is possible that a material that causes fogging when tested alone will not have an adverse effect when a small amount is in a blend. Since single materials do not allow the diversity of aromas characteristic of commercial fragrances, the examples show simple blends that allow the creation of a variety of odors. The examples are constructed totally of nonfogging materials. The solvents allow cost reduction, dilution of strong odorants, and prevention of freezing in frigid climates.

THE INVENTION

Objective of the Invention

It is the objective of the present invention to provide fragrance compositions and a method of delivering them that are chemically uniform, oxidatively stable, and are non-fogging on automotive glass.

Summary of the Invention

Fragrances consist of a diverse mixture of chemical types, including hydrocarbons, alcohols, esters, aldehydes and ketones, heterocyclics, Schiff bases, and phenols. Natural products consisting of complex mixtures are used, such as citrus and flower oils. In addition to aroma chemicals, solvents and surfactants are often included in fragrance compositions to reduce cost, dissolve solid materials, or modify the solubility characteristics: examples are dipropylene glycol, diethylene glycol, benzyl benzoate, polysorbate 20 and nonoxynol 9.

To satisfy this invention, aroma materials must be selected either individually or in combination which produce pleasant scents or which can help mask unpleasant odors such as smoke and decaying food. In addition, fragrances having desired properties as determined by studies in aromachology will have special value.

Studies have proven that fragrances can effect mood and alertness, based on the transmission of olfactory information to the limbic system of the brain. In particular, research has shown that aromas can increase driver awareness and thus enhance safety. This invention includes specific materials of functional as well as aesthetic value.

The fragrance compositions useful in the practice of the present invention are composed of (a) solvents, (b) aroma chemicals and (c) surfactants. In order to be useful in the practice of the present invention, each component must pass SAE-J1756 having a minimum fog number of 60. Within the broad guidelines of SAE-J1756, individual vehicle manufacturers have specified exact criteria.

Several series of fogging tests on aroma chemicals and solvents have been performed (Reliable Analysis, Troy, Mich.). To conform as closely as possible to automotive requirements, General Motors test procedure GM9305P was employed. Samples were subjected to 95° C. for 6 hours in a Hart Fog Chamber (Model 0011, S/N 125) and a 38° C. cooling plate. The samples were conditioned for 16 hours in the laboratory environment. Gloss measurements were made (BYK-Gardner Micro TRI Gloss Meter), and microscopic examination (40× magnification) performed. A minimum fogging number of 60 was required. Test materials can fail for a high fog number, the presence of droplets, or crystal formation Examples of functional examples of materials that pass the test were d'limonene, methyl hexyl ketone, phenylethyl alcohol, lillial and verdox. Examples of solvents that passed the test were DUP (diundecyl phthalate) and TOTM (trioctyl trimellitate). The materials that passed are important for the purposes of this invention because they allow the creation of a citrus or floral fragrance, and the solvents are such as to prevent solidification of the fragrance in frigid environments.

Examples of materials failing the test are Suederal® S (IFF), helional®, citronellol, DPG (dipropylene glycol) and linalool. Suederal® is a leather chemical specialty, and DPG is the most common fragrance solvent. The tests indicate the difficulty of incorporating a leather fragrance, typical of "new car smell" into a vehicle. The tests also indicate that chemical types or odor types do not give predictable results. Some aldehydes pass while other aldehydes fail. Similarly, certain citrus notes pass while others fail. Testing each raw material is necessary to assemble a technically acceptable fragrance.

Formulas of standard fragrance types passing the fogging test are:

| Citrus Blend | |
|---|---|
| D'limonene | 50–100% |
| Tangerine Oil | 0–25% |
| Lilial | 0–30% |
| DUP | 0–80% |
| TOTM | 0–80% |
| Floral Blend | |
| Lilial | 70–100% |
| Phenylethyl alcohol | 0–30% |
| Methyl Hexyl Ketone | 0–15% |
| DUP | 0–80% |
| TOTM | 0–80% |

In addition to fogging, oxidative stability is important for long term odor value. This invention suggests, but is not limited to, a system by which the fragrance be dispensed by mechanical pump or venturi valve from a sealed can similar to that commonly used for aerosols. In place of the propellant, a blanket of inert gas such a nitrogen will replace the air in a purged container, eliminating the presence of oxygen. Tests conducted on d'limonene in a glass bottle and sealed container at elevated temperatures confirmed the benefit of this method. The addition of antioxidants such as BHT (butylated hydroxytoluene) to this system is suggested for improved stability. This sealed container will also prevent the fragrance system from contributing to the EPA Diurnal Emission Test.

We claim:

1. A process for providing a chemically uniform fragrance composition into a automobile that does not deposit on automotive glass which comprises spraying a composition consisting of fragrance compounds and solvent compounds having an fog value of 60 or above, dispensed from a sealed container under a blanket of inert gas.

2. A process of claim 1 wherein said fragrance compound is selected from the group consisting of d'limonene, methyl hexyl ketone, phenylethyl alcohol, lillial, verdox, diundecyl phthalate, and trioctyl trimellitate.

3. A process of claim 1 wherein said fragrance compound is d'limonene.

4. A process of claim 1 wherein said fragrance compound methyl hexyl ketone.

5. A process of claim 1 wherein said fragrance compound phenylethyl alcohol.

6. A process of claim 1 wherein said fragrance compound lillial.

7. A process of claim 1 wherein said fragrance compound verdox.

8. A process of claim 1 wherein said fragrance compound diundecyl phthalate.

9. A process of claim 1 wherein said fragrance compound trioctyl trimellitate.

* * * * *